(12) United States Patent
Salter et al.

(10) Patent No.: US 10,960,134 B2
(45) Date of Patent: Mar. 30, 2021

(54) TUBE CRIMPING ARRANGEMENT FOR DRUG DELIVERY DEVICE

(71) Applicant: Becton, Dickinson and Company, Franklin Lakes, NJ (US)

(72) Inventors: Jamie Anthony Salter, Chesham (GB); Oliver Charles Gazeley, Leamington Spa (GB); David Aubrey Plumptre, Droitwich (GB); James Alexander Senior, Warwick (GB); Gareth James Lewis, High Wycombe (GB); Malcolm Stanley Boyd, Wellesbourne (GB); Javier Eduardo Nadal, Warwick (GB)

(73) Assignee: Becton, Dickinson and Company, Franklin Lakes, NJ (US)

( * ) Notice: Subject to any disclaimer, the term of this patent is extended or adjusted under 35 U.S.C. 154(b) by 297 days.

(21) Appl. No.: 16/160,184

(22) Filed: Oct. 15, 2018

(65) Prior Publication Data

US 2019/0111207 A1    Apr. 18, 2019

Related U.S. Application Data

(60) Provisional application No. 62/572,692, filed on Oct. 16, 2017.

(51) Int. Cl.
*A61M 5/168* (2006.01)
*A61M 5/145* (2006.01)
(Continued)

(52) U.S. Cl.
CPC ...... *A61M 5/16813* (2013.01); *A61M 5/1454* (2013.01); *A61M 5/14244* (2013.01);
(Continued)

(58) Field of Classification Search
CPC .......... A61M 5/14248; A61M 5/14244; A61M 5/1454; A61M 5/158; A61M 5/16881; A61M 2005/14252; A61M 2005/1585
See application file for complete search history.

(56) References Cited

U.S. PATENT DOCUMENTS 6,749,587 B2 * 6/2004 Flaherty ................. A61P 25/04
                                              604/151
7,951,122 B2    5/2011 Shekalim
(Continued)

FOREIGN PATENT DOCUMENTS

AU    2010207762 A1   9/2010
EP       1884259 A1   2/2008
(Continued)

*Primary Examiner* — Nathan R Price
*Assistant Examiner* — Melissa A Snyder
(74) *Attorney, Agent, or Firm* — The Webb Law Firm

(57) ABSTRACT

A drug delivery system for injecting a medicament is provided. The system includes a container configured to receive a medicament; a drive assembly which, upon actuation, is configured to expel the medicament from the container; a needle for injecting the medicament to a patient; a fluid path assembly comprising a tube in fluid communication with the container and the needle for conducting fluid from the container to the needle; and a tube crimping arrangement configured to engage the tube to block fluid flow through the tube. The drive assembly causes the tube crimping arrangement to engage the tube after a dose of the medicament has been delivered to the patient through the needle.

14 Claims, 15 Drawing Sheets

(51) Int. Cl.
  *A61M 5/158* (2006.01)
  *A61M 5/142* (2006.01)
  A61M 5/20 (2006.01)
  A61M 5/31 (2006.01)

(52) U.S. Cl.
  CPC ........ *A61M 5/14248* (2013.01); *A61M 5/158* (2013.01); *A61M 5/16881* (2013.01); *A61M 5/2033* (2013.01); *A61M 2005/14256* (2013.01); *A61M 2005/14506* (2013.01); *A61M 2005/1585* (2013.01); *A61M 2005/3103* (2013.01)

(56)  References Cited

U.S. PATENT DOCUMENTS

| | | |
|---|---|---|
| 8,021,357 B2 | 9/2011 | Tanaka et al. |
| 2005/0203461 A1* | 9/2005 | Flaherty ............ A61M 5/14248 604/131 |
| 2015/0080800 A1 | 3/2015 | Cronenberg |
| 2016/0058941 A1 | 3/2016 | Wu et al. |
| 2017/0028132 A1 | 2/2017 | Cronenberg et al. |

FOREIGN PATENT DOCUMENTS

| | | |
|---|---|---|
| WO | 2008139464 A1 | 11/2008 |
| WO | 2013155153 A1 | 10/2013 |
| WO | 2014179774 A1 | 11/2014 |
| WO | 2015081337 A2 | 6/2015 |

* cited by examiner

TUBE CRIMPING ARRANGEMENT FOR DRUG DELIVERY DEVICE

CROSS-REFERENCE TO RELATED APPLICATIONS

This application claims priority to U.S. Provisional Application Ser. No. 62/572,692 filed Oct. 16, 2017, entitled "Tube Crimping Arrangement for Drug Delivery Device", the entire disclosure of which is hereby incorporated by reference.

BACKGROUND OF THE INVENTION

Field of the Disclosure

The present disclosure relates generally to a drug delivery or injector device and method for delivering a fluid into the body of a patient by injection and, in particular, to a drug delivery device configured to automatically provide a fluid lock to prevent fluid from leaking from the device after fluid delivery is completed.

Description of the Related Art

Various types of automatic injection devices have been developed to allow drug solutions and other liquid therapeutic preparations to be administered by untrained personnel or to be self-injected. Generally, these devices include a reservoir that is pre-filled with the liquid therapeutic preparation, and some type of automatic needle-injection mechanism that can be triggered by the user. When the volume of fluid or drug to be administered is generally below a certain volume, such as 1 mL, an auto-injector is typically used, which typically has an injection time of about 10 to 15 seconds. When the volume of fluid or drug to be administered is above 1 mL, the injection time generally becomes longer resulting in difficulties for the patient to maintain contact between the device and the target area of the patient's skin. Further, as the volume of drug to be administered becomes larger, increasing the time period for injection becomes desirable. The traditional method for a drug to be injected slowly into a patient is to initiate an IV and inject the drug into the patient's body slowly. Such a procedure is typically performed in a hospital or outpatient setting.

Certain devices allow for self-injection in a home setting and are capable of gradually injecting a liquid therapeutic preparation into the skin of a patient. In some cases, these devices are small enough (both in height and in overall size) to allow them to be "worn" by a patient while the liquid therapeutic preparation is being infused into the patient. These devices typically include a pump or other type of discharge mechanism to force the liquid therapeutic preparation to flow out of a reservoir and into the injection needle. Such devices also typically include a valve or flow control mechanism to cause the liquid therapeutic preparation to begin to flow at the proper time and a triggering mechanism to initiate the injection.

SUMMARY OF THE INVENTION

According to an aspect of the disclosure, a drug delivery system for injecting a medicament is provided. The system includes: a container configured to receive a medicament; a drive assembly which, upon actuation, is configured to expel the medicament from the container; a needle for injecting the medicament to a patient; a fluid path assembly comprising a tube in fluid communication with the container and the needle for conducting fluid from the container to the needle; and a tube crimping arrangement configured to engage the tube to block fluid flow through the tube. The drive assembly causes the tube crimping arrangement to engage the tube after a dose of the medicament has been delivered to the patient through the needle.

In some examples, upon actuation, the drive assembly automatically causes the tube crimping arrangement to engage the tube. Optionally, the system further comprises a housing enclosing at least a portion of the container, drive assembly, needle, fluid path assembly, and tube crimping arrangement. The housing can include a top cover engaged to a bottom cover.

In some examples, the system further includes a needle actuator assembly having a movable portion biased by a biasing member and configured to move the needle between a pre-use position, a use position for delivery of the medicament to the patient, and a post-use position after delivery of the medicament is completed. Optionally, the system further includes a housing enclosing at least a portion of the container, drive assembly, needle, fluid path assembly, and tube crimping arrangement. The needle can be retracted into the housing in the pre-use and post use positions. At least a portion of the needle can be extended from the housing in the use position.

In some examples, transition of the needle actuator assembly between the use position and the post-use position causes the tube crimping arrangement to engage the tube. For example, upon actuation, the drive assembly can automatically cause the needle actuator assembly to transition the needle between the use position and the post-use position.

In some examples, the tube crimping arrangement includes at least one tube crimping member configured to be driven toward the tube by contact with the movable portion of the needle actuation assembly. Optionally, the system further includes a housing enclosing at least a portion of the container, drive assembly, needle, and fluid path assembly. The at least one crimping member can include one or more flexible blades pivotally mounted to a portion of the housing. The movable portion of the needle actuator assembly can include one or more pins extending therefrom. The pins can be configured to contact the flexible blades to drive the flexible blades towards the tube.

In some examples, the system further includes a housing enclosing at least a portion of the container, drive assembly, needle, and fluid path assembly. The at least one crimping member can include two flexible blades pivotally mounted to a portion of the housing and defining a gap therebetween. The movable portion of the needle actuator assembly can include a first set of pins positioned to deflect the two flexible blades away from one another to expand the gap and a second set of pins positioned to drive the two flexible blades towards one another to contact the tube. Optionally, the movable portion of the needle actuator assembly includes a ridge configured to press the tube into the gap when the gap is expanded by contact between the first set of pins and the flexible blades.

In some examples, the biasing member of the needle actuator assembly exerts a force of 1 N or less on the tube crimping arrangement. In some examples, the tube is a flexible single walled tube having a diameter of 0.7 mm or less.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein.

Corresponding reference characters indicate corresponding parts throughout the several views. The exemplifications set out herein illustrate exemplary aspects of the disclosure, and such exemplifications are not to be construed as limiting the scope of the disclosure in any manner.

DETAILED DESCRIPTION

Figure 1:
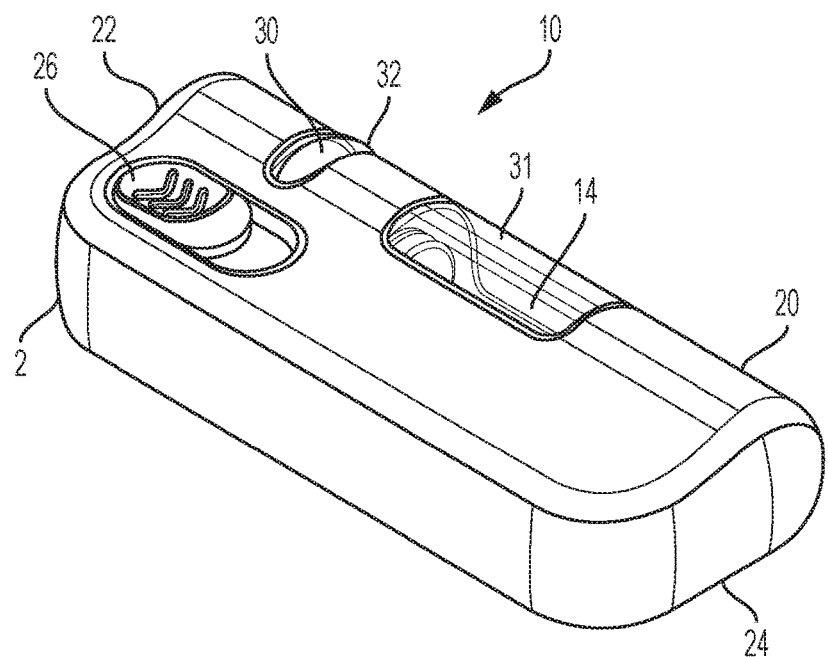
FIG. 1 is a perspective view of a drug delivery system according to one aspect of the present invention.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

A drug delivery system including an injector device for injecting a fluid medicament to a patient is provided. The injector device can be configured to provide injection of a fluid substance over a predetermined time period. The injector device can be wearable and configured to be affixed to a patient. In some examples, the injection can occur automatically meaning that, once the user actuates the system or device, the injection occurs without further action by the patient. In some instances, the injector device includes a drive mechanism that transitions the device between a pre-use position, a use-position, and a post-use position. For example, transitioning the injector device through the various positions can include causing a needle to extend from the device and to be inserted into the patient, expelling fluid medicament from a container or reservoir of the injector device to the patient through the needle, and retracting the needle back into the device for safe disposal. The injector device can include a cover or pad for covering the tip of the needle after the injection is completed to prevent fluid leaks.

In some examples, the injector device includes a fluid path assembly for transporting fluid through the injector device. The fluid path assembly can include a flexible tube or conduit for transporting fluid from the container or reservoir to the needle. In some examples, the injector device includes a tube crimping arrangement that is configured to achieve fluid lock of the tube or conduit after the injection is completed (e.g., end-of-dose). The fluid lock can supplement protection provided by the needle pad or cover and, in particular, can prevent fluid from leaking or flowing from the injector device once an injection is completed. The tube crimping arrangement can be integrated with other biasing or movement mechanisms of the injector device, such that the tube is automatically crimped to prevent fluid leak at the end-of-dose. For example, movement of the drive mechanism to transition the device between the use and post-use positions can actuate the tube crimping mechanism, as discussed herein, by driving crimping or clamping structures against the tube or conduit to compress the tube or conduit and to prevent fluid flow therethrough.

Exemplary Fluid Delivery System

As shown in FIGS. 1-12, a drug delivery system 10 according to one aspect of the present invention includes an injector device 2 having a drive assembly 12 (shown in FIGS. 2-8), a container 14, a valve assembly 16 (shown in FIGS. 2, 4, 5, 7, and 10), a needle actuator assembly 18 (shown in FIGS. 2-8, and a fluid path assembly 200 (shown, example, in FIG. 12) for conducting fluid from the valve assembly 16 to a needle 28 (shown in FIGS. 3, 6, and 8) of the needle actuator assembly 18. The drive assembly 12, the container 14, the valve assembly 16, the needle actuator assembly 18, and the fluid path assembly 200 are at least partially positioned within a housing 20.

As shown in FIG. 1, the housing 20 is formed from a top cover 22 and a bottom cover 24, although other suitable arrangements for the housing 20 may be utilized. In one aspect, the injector device 2 is configured to be worn or secured to a user and to deliver a predetermined dose of a medicament provided within the container 14 via injection to the patient. The drug delivery system 10 and injector device 2 may be utilized to deliver a "bolus injection" where a medicament is delivered within a set time period. The medicament may be delivered over a time period of up to 45 minutes, although other suitable injection amounts and durations may be utilized. A bolus administration or delivery can be carried out with rate controlling or have no specific rate controlling. The system 10 and injector device 2 may deliver the medicament at a fixed pressure to the user with the rate being variable.

The injector device 2 is configured to operate by engagement (e.g., depressing and/or sliding) of an actuation button 26 by a patient. Engagement of the button 26 causes the needle 28 (shown in FIGS. 3, 6, and 8) of the needle assembly 18 to extend from the housing 20 and to pierce the skin of the patient. Engagement of the button 26 also actuates the drive assembly 12 via the needle actuator (shown in FIGS. 2-12), which places the needle 28 in fluid communication with the container 14 through a flexible tube 210 of the fluid path assembly 200 (shown, for example, in FIG. 12). Once the container 14 is in fluid communication with the needle 28, the drive assembly 12 expels fluid or medicament from the container 14 and to the patient through the needle 28. Once a total desired dose is delivered to the patient, the drive assembly 12 in conjunction with the needle actuator, needle actuator spring, and release flipper causes the needle 28 to withdraw from the user and to recede into the housing 20. General operation of an exemplary drug delivery system is shown and described in International Publication Nos. WO 2013/155153 and WO 2014/179774, which are hereby incorporated by reference in their entirety. Additionally, in some configurations, the container 14 and valve assembly 16 may be the container and valve assembly shown and described in International Publication No. WO 2015/081337, which is also hereby incorporated by reference in its entirety.

With continued reference to FIG. 1, in some examples, the housing 20 of the system 10 includes an indicator window 30 for viewing an indicator arrangement 32 configured to provide an indication to a user on the status of the system 10 and a container window 31 for viewing the container 14. The indicator window 30 may be a magnifying lens for providing a clear view of the indicator arrangement 32. In some examples, the indicator arrangement 32 moves along with the needle actuator assembly 18 during use of the system 10 to indicate a pre-use position, use position, and post-use position of the system 10 and device 2. The indicator arrangement 32 provides a visual indication regarding the device status. As will be appreciated by those of ordinary skill in the art, other suitable indicators, such an auditory or tactile indicators, may be provided as an alternative or in addition to the visual indication provided by the indicator arrangement 32.

Figure 2:
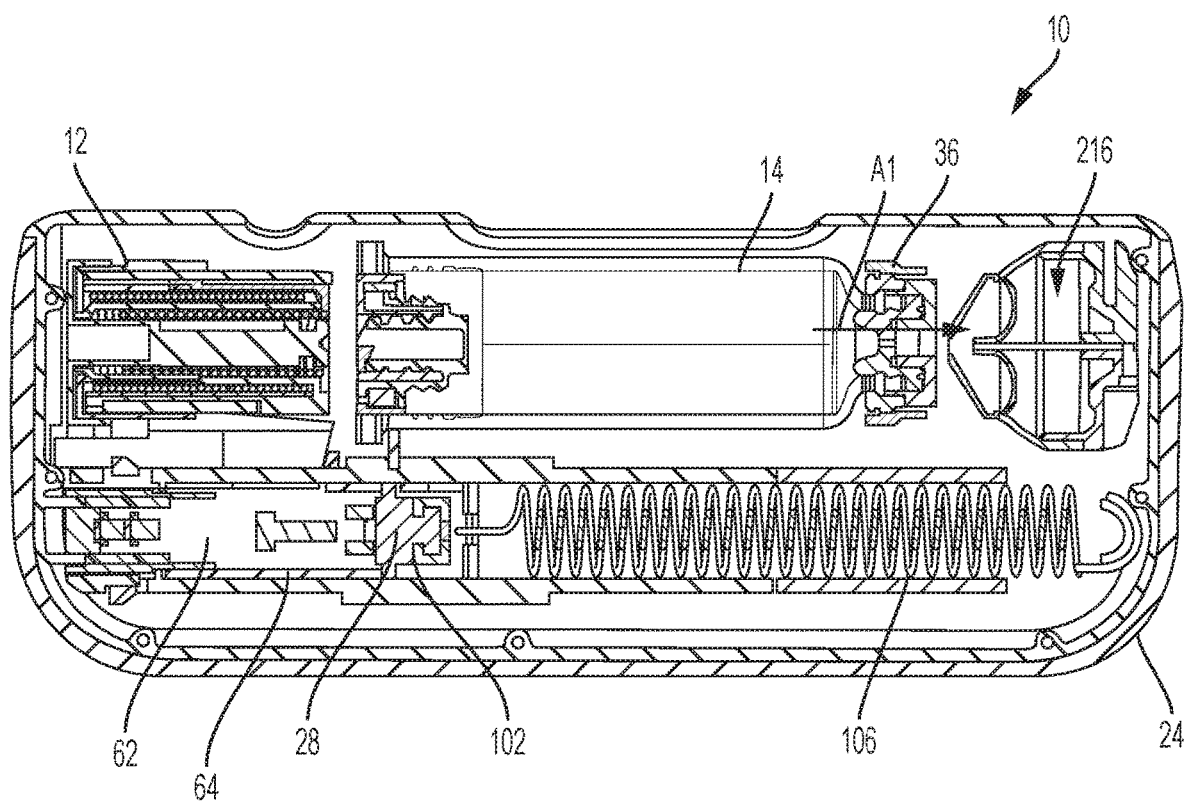
FIG. 2 is a top view of the drug delivery system of FIG. 1 according to one aspect of the present invention, showing a top cover of the housing removed and the drug delivery system in a pre-use position.
Figure 3:
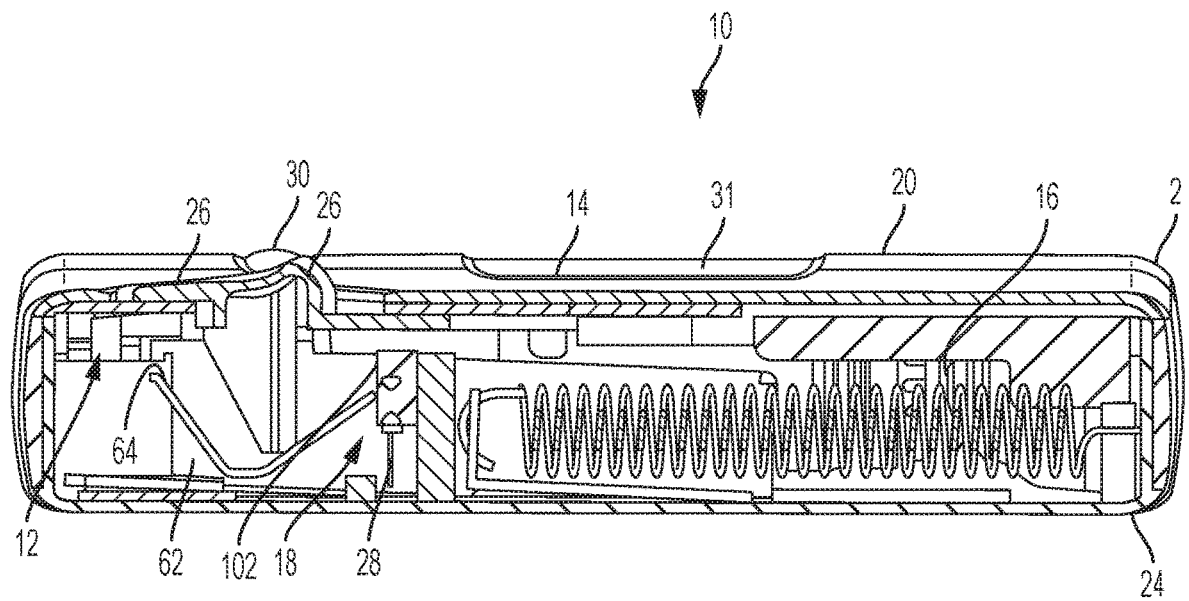
FIG. 3 is a front, cross-sectional view of the drug delivery system of FIG. 1 according to one aspect of the present invention, showing the drug delivery system in a pre-use position.

As shown in FIGS. 2 and 3, during a pre-use position of the injector device 2, the container 14 is spaced from the drive assembly 12 and the valve assembly 16 and the needle 28 is in a retracted position. The drive assembly 12 is configured to engage a stopper 34 of the container 14 via a spacer component, which will initially move the entire container 14 into engagement with the valve assembly 16, in the direction of arrow A1 (shown in FIG. 2) due to the incompressibility of the fluid or medicament within the container 14.

Figure 4:
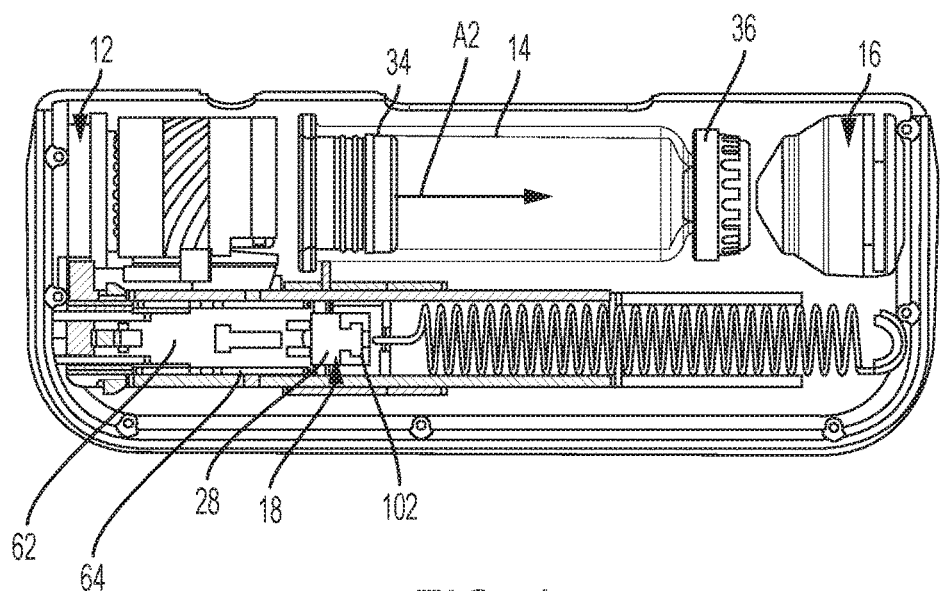
FIG. 4 is a top view of the drug delivery system of FIG. 1 according to one aspect of the present invention, showing a top cover of the housing removed and the drug delivery system in an initial actuation position.
Figure 12:
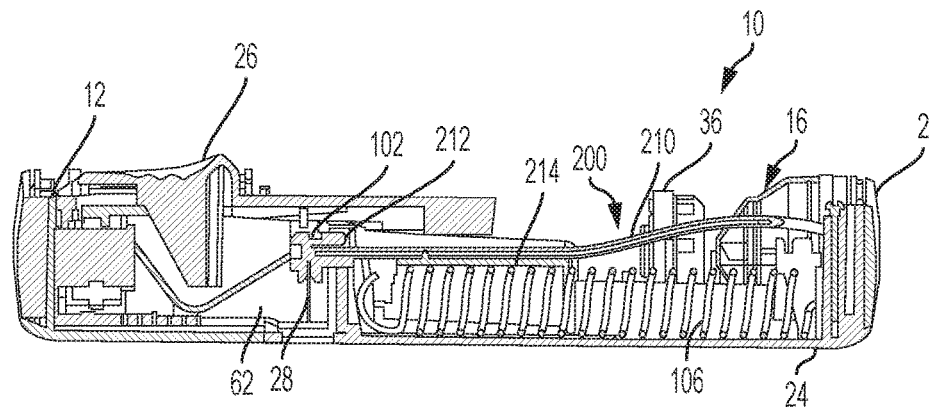
FIG. 12 is a front, cross-sectional view of the drug delivery system of FIG. 1 according to one aspect of the present invention, showing the fluid path assembly and the drug delivery system in a pre-use position

More specifically, during the initial actuation of the injector device 2, as shown in FIG. 4, the drive assembly 12 engages the container 14 to move the container 14 toward the valve assembly 16, which is configured to pierce a closure 36 of the container 14 and place the medicament within the container 14 in fluid communication with the needle 28 via the fluid path assembly 200 (shown in FIG. 12). The initial actuation of the system 10 is caused by engagement of the actuation button 26 by a user (e.g., the patient or a caregiver), which releases the needle actuator assembly 18 and the drive assembly 12 as discussed below in more detail. During the initial actuation, the needle 28 is still in the retracted position and about to move to the extended position to inject the user of the system 10.

Figure 5:
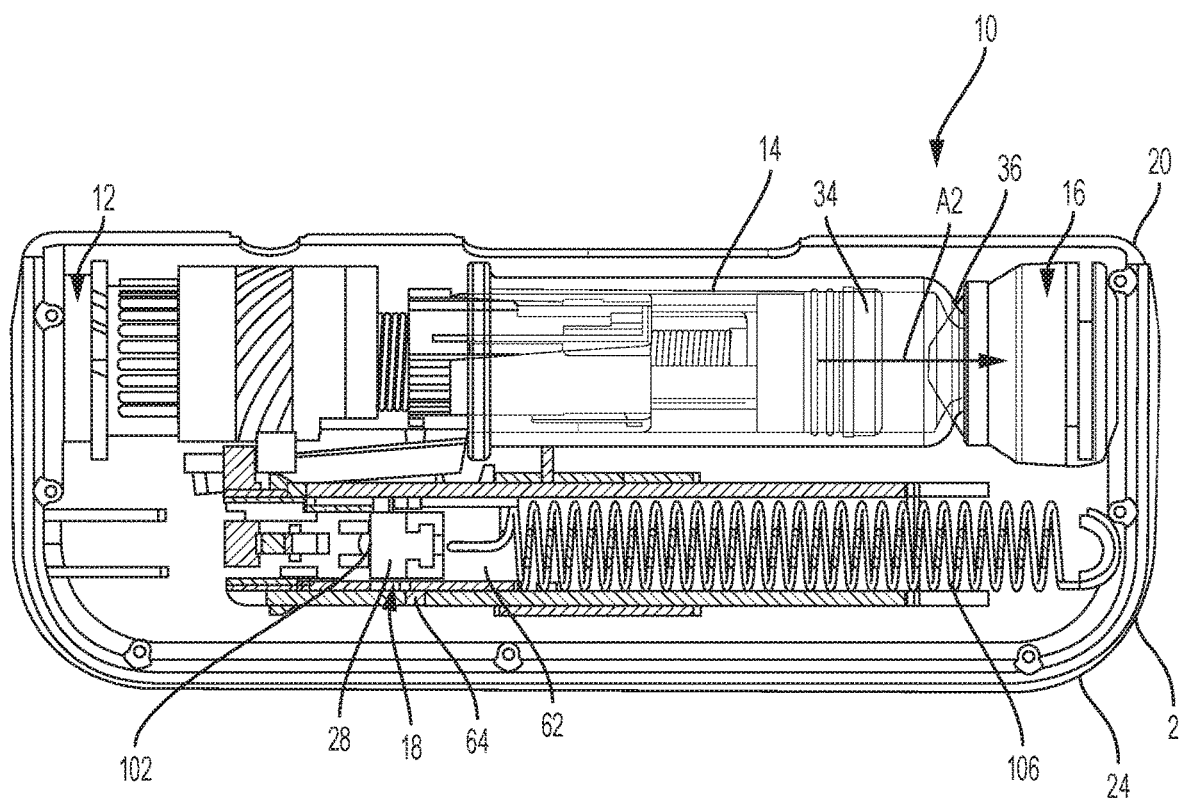
FIG. 5 is a top view of the drug delivery system of FIG. 1 according to one aspect of the present invention, showing a top cover of the housing removed and the drug delivery system in an in use position.
Figure 6:
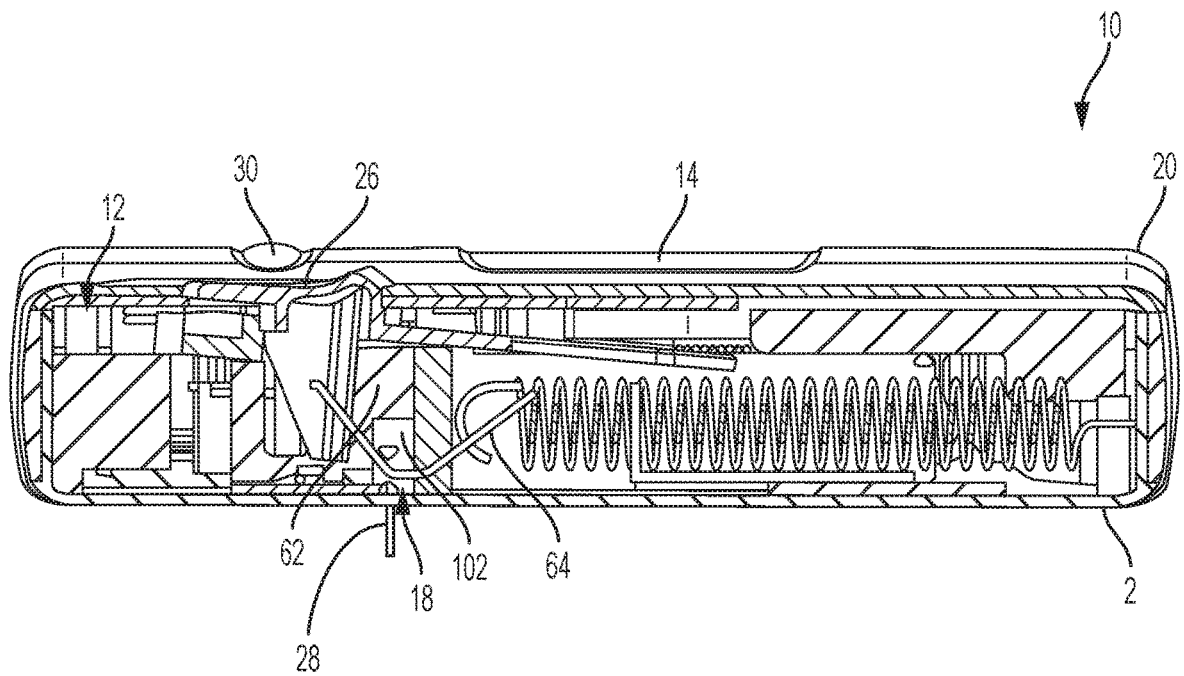
FIG. 6 is a front, cross-sectional view of the drug delivery system of FIG. 1 according to one aspect of the present invention, showing the drug delivery system in an in use position.

When the device 2 transitions to the use position, as shown in FIGS. 5 and 6, the needle 28 is in the extended position, at least partially outside of the housing 20, with the drive assembly 12 moving the stopper 34 within the container 14 to deliver the medicament from the container 14, through the needle 28, and to the patient. In the use position, the valve assembly 16 has already pierced the closure 36 of the container 14 to place the container 14 in fluid communication with the needle 28, which also allows the drive assembly 12 to move the stopper 34 relative to the container 14, as shown by arrow A2 (in FIGS. 4 and 5) since fluid is able to be dispensed from the container 14.

Figure 7:
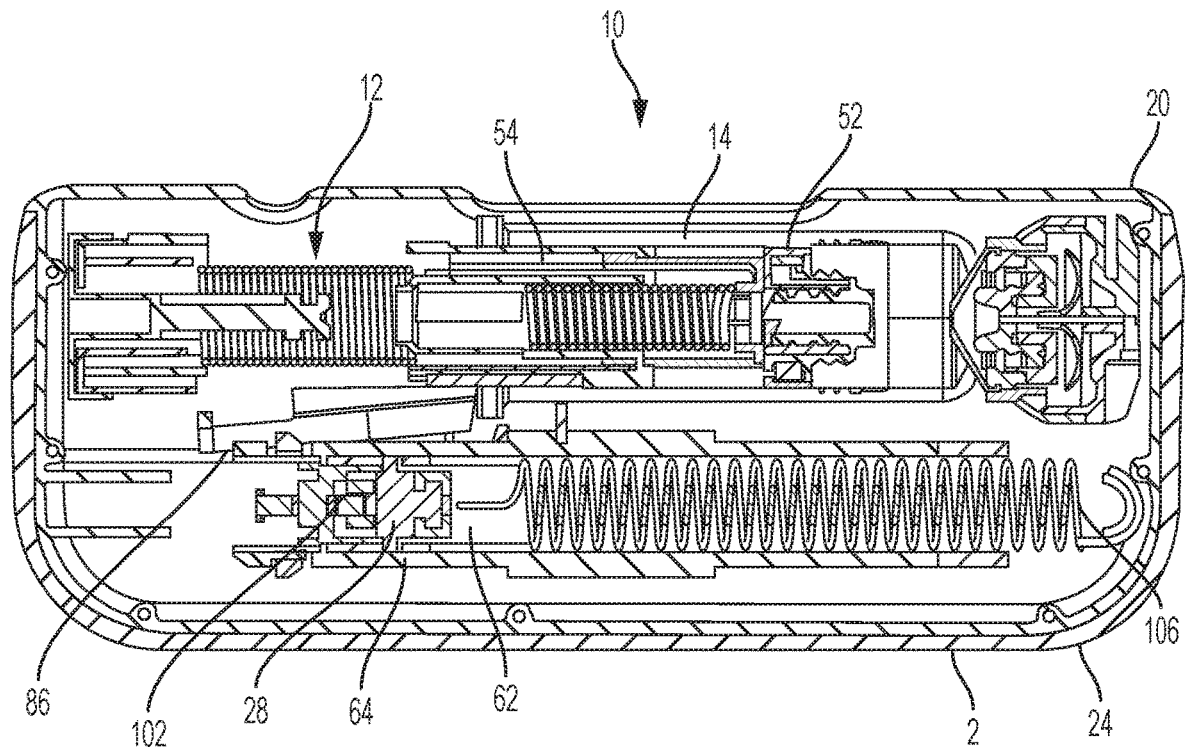
FIG. 7 is a top view of the drug delivery system of FIG. 1 according to one aspect of the present invention, showing a top cover of the housing removed and the drug delivery system in a post-use position.
Figure 8:
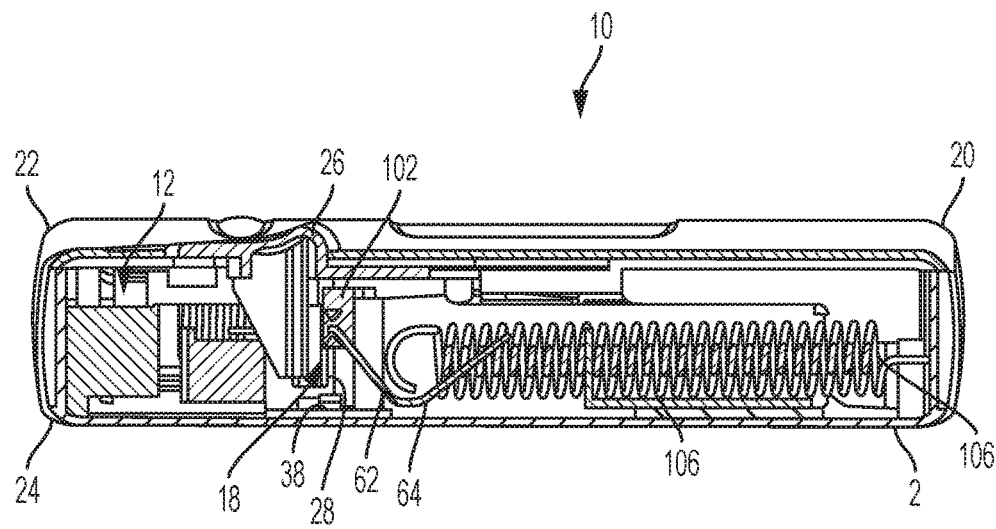
FIG. 8 is a front, cross-sectional view of the drug delivery system of FIG. 1 according to one aspect of the present invention, showing the drug delivery system in a post-use position.

At the post-use position of the injector device 2, shown in FIGS. 7 and 8, the needle 28 (shown in FIG. 8) is in the retracted position and engaged with a pad 38 to seal the needle 28 and prevent any residual flow of fluid or medicament from the container 14. In addition, as discussed hereinafter, a tube crimping mechanism 202 (shown in FIGS. 13-18) of the fluid path assembly 200 (shown, for example, in FIG. 12) crimps or clamps against the tube 210 to provide a fluid lock, which blocks fluid from passing through the tube 210 and to the needle 28. In some examples, the tube crimping arrangement 202 is driven by the drive mechanism 12 and/or by movement of other portions of the device which translate through the housing 20 as the device 2 transitions from the use-position to the pose-use position.

Drive Assembly

Referring to FIGS. 2-8, the drive assembly 12 according to one aspect of the present invention is shown. As discussed above, the drive assembly 12 is configured to move the container 14 in the direction of arrow A1 (shown in FIG. 2), to pierce the closure 36 of the container 14 and also to move the stopper 34 within the container 14 in the direction of arrow A2 (shown in FIGS. 4 and 5) to dispense fluid or medicament from the container 14. In some examples, the drive assembly 12 can be configured to dispense a plurality of discrete fill volume ranges. For example, the drive assembly 12 can include a number of stops or spacers for restricting or limiting translation of the drive assembly 12 through the housing 20, thereby limiting the amount of fluid expelled from the container 14. In one example, the injector device 2 can be capable of delivering thirteen discrete fluid volumes or doses to the patient. A desired injection volume can be selected prior to device assembly and the drive assembly assembled in this configuration.

Figure 9A:
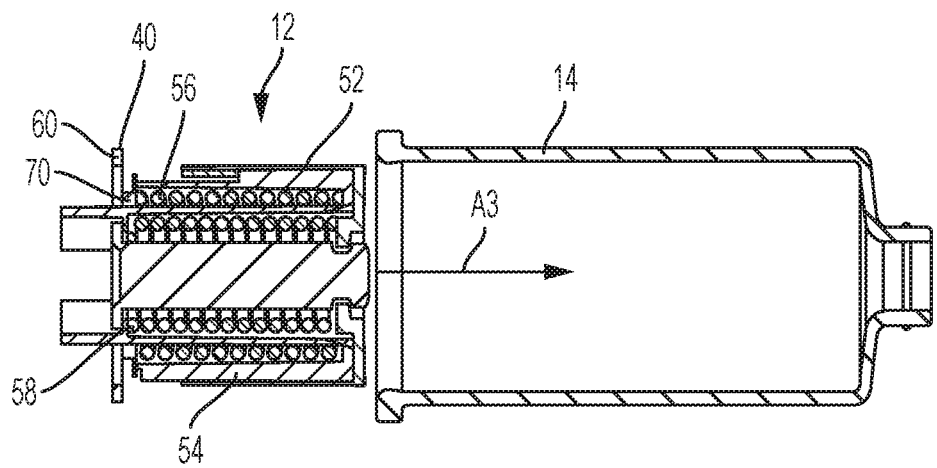
FIG. 9A is a cross-sectional view of a drive assembly of the drug delivery system of FIG. 1 according to one aspect of the present invention, showing a pre-use position of the drive assembly.
Figure 9B:
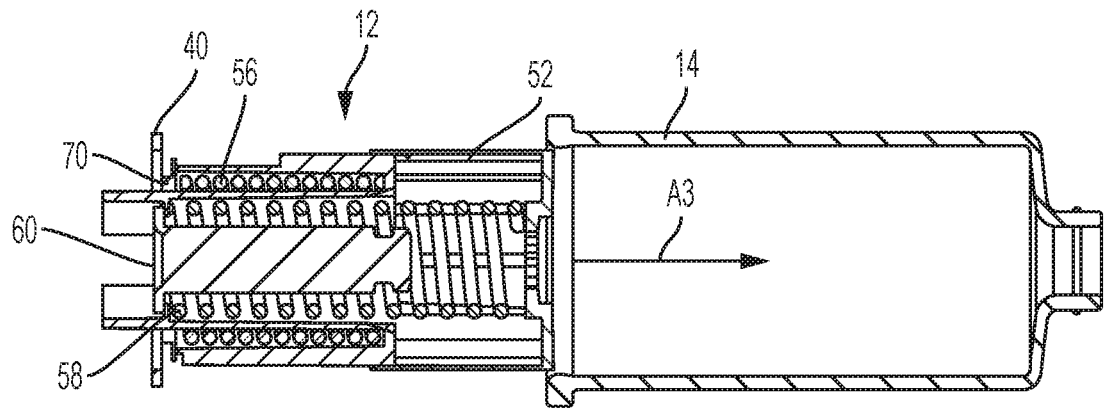
FIG. 9B is a cross-sectional view of the drive assembly of FIG. 9A according to one aspect of the present invention, showing a use position of the drive assembly.
Figure 9C:
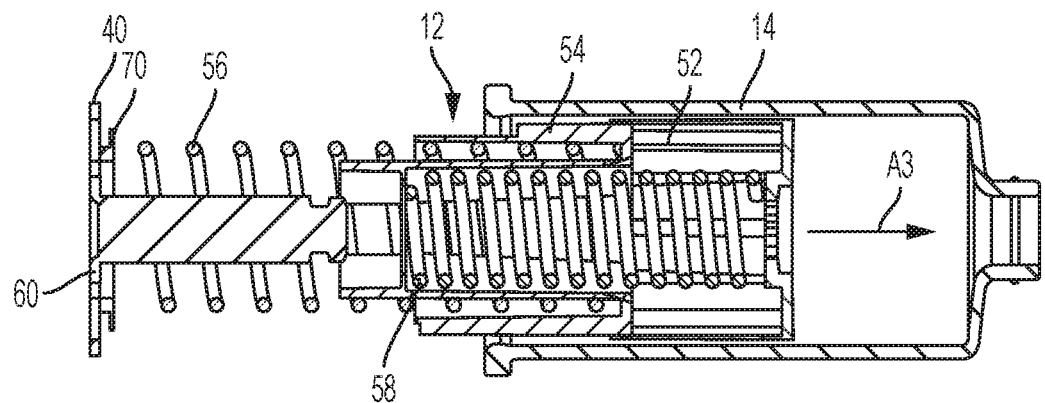
FIG. 9C is a cross-sectional view of the drive assembly of FIG. 9A according to one aspect of the present invention, showing a post-use position of the drive assembly.

With reference to FIGS. 9A-9C, elements of the drive assembly 12 which advance a plunger member 52 through the container 14 are shown in detail. In some examples, the drive assembly 12 includes the first plunger member 52, a second plunger member 54 received by the first plunger member 52, a first biasing member 56, a second biasing member 58, a plunger actuation member 60, and an index member 70. The first plunger member 52 is moveable from the pre-use position (shown in FIG. 9A), to the use position (shown in FIG. 9B), to the post-use position (shown in FIG. 9C) with the first plunger member 52 configured to move the stopper 34 (shown in FIGS. 2-8) within the container 14 to dispense medicament from the container 14. The first plunger member 52 is configured to move axially. The second plunger member 54 and the first plunger member 52 form a telescoping arrangement with the second plunger 54 configured to move axially after the first plunger member 52 moves a predetermined axial distance. The movement of the first and second plunger members 52, 54 is provided by the first and second biasing members 56, 58, which are compression springs, although other suitable arrangements for the biasing members 56, 58 may be utilized.

A drive surface 40 of the plunger actuation member 60 is configured to be engaged by a portion of the needle actuator assembly 18 (shown in FIGS. 2-8) to effect movement of the needle actuator assembly 18 through the housing 20 (shown in FIGS. 2-9) as the injector device 2 transitions from the pre-use position, to the use position, to the post use position. For example, after engagement of the actuator button 26 and release of the needle actuator assembly 18, the needle actuator assembly 18 moves within the housing 20 in the direction of arrow A3 (in FIGS. 9A-9C). During the initial movement of the needle actuator assembly 18, a portion of the needle actuator assembly 18 engages the drive surface 40 of the plunger actuation member 60 to move the plunger actuation member 60 from the first rotational position to the second rotational position.

With reference again to FIG. 7, the second plunger member 54 is configured to engage a restriction member 86 of the system 10. The restriction member 86 cooperates with the needle actuation assembly 18 and restricts movement of the needle actuator assembly 18 from the use position to the post-use position until a predetermined end-of-dose position of the stopper 34 is reached. Such engagement between the restriction member 86 and the needle actuation assembly 18 is released by rotation of the restriction member 86 when the stopper 34 reaches its end-of-dose position. During the use position of the needle actuator assembly 18, the restriction member 86 is biased in a rotational direction with the rotation of the restriction member 86 being prevented through engagement with the second plunger member 54.

Figure 10:
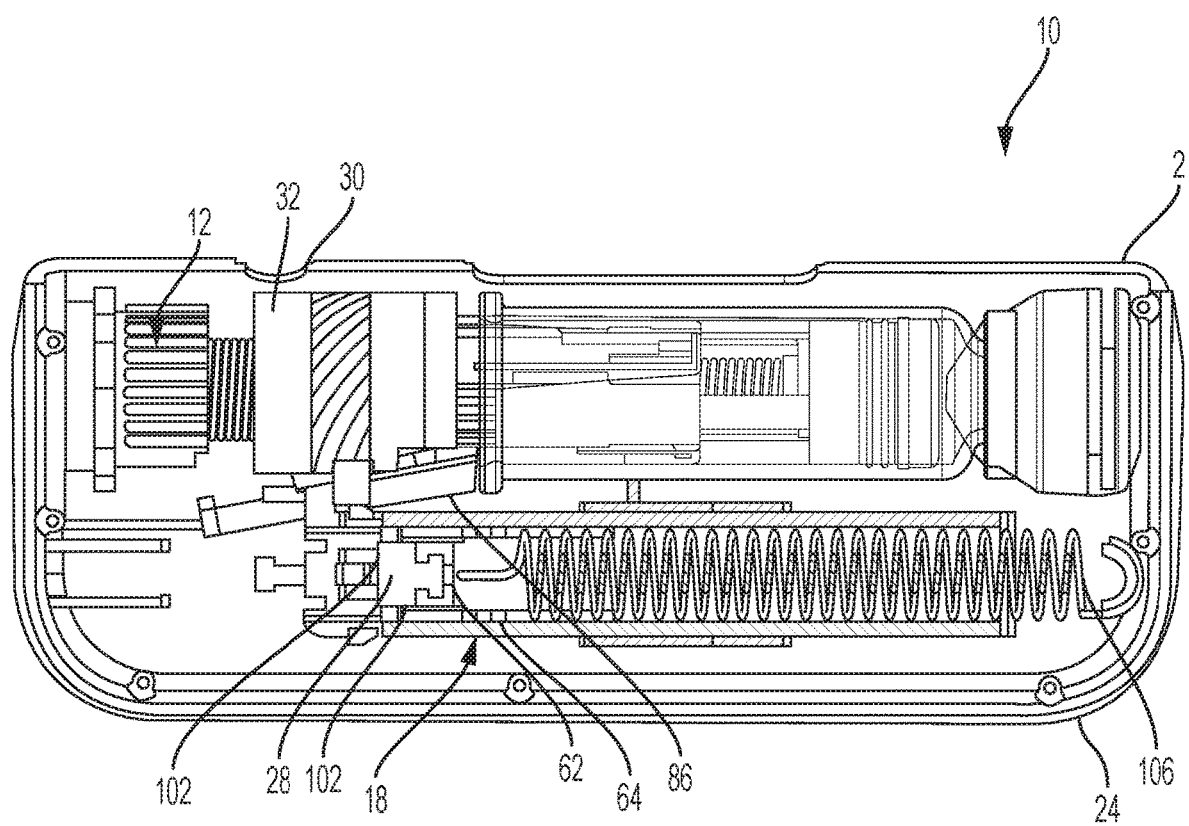
FIG. 10 is another top view of the drug delivery system of FIG. 1 according to one aspect of the present invention, showing a top cover of the housing removed and the drug delivery system in a post-use position.
Figure 11:
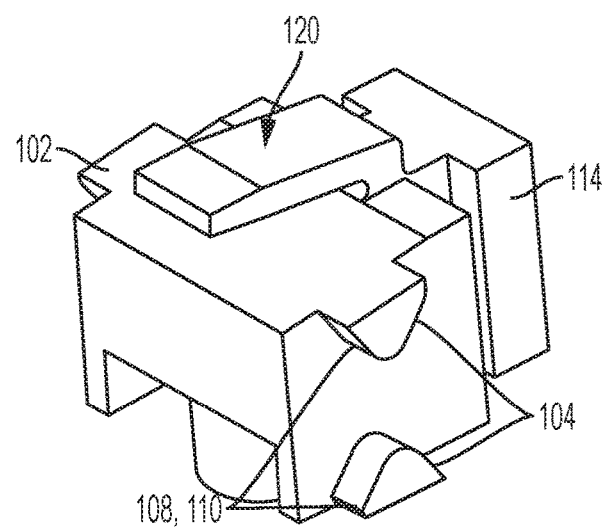
FIG. 11 is a left side perspective view of a needle shuttle of a needle actuator assembly of the drug delivery system of FIG. 1 according to one aspect of the present invention.

With reference to FIG. 10, in some examples, the restriction member in conjunction with the needle actuator is also configured to adjust the position of the indicator arrangement 32 to identify for the user or patient the status of the injection (e.g., pre-use, injection occurring, post-use or end-of-dose). Movement of the indicator arrangement 32 can be viewed through the window 30. More specifically, as shown in FIG. 10, the indicator arrangement 32 engages a portion of the restriction member 86 and moves along with the restriction member 86 to reach the first state and then the indicator arrangement engages a portion of the needle actuator and moves along with the needle actuator to reach the final state of the system. Movement of the restriction member 86 can, for example, rotate the indicator arrangement 32 to provide an indication to the user regarding the state of the system 10.

Needle Actuator Assembly

Referring to FIGS. 2-10, the needle actuator assembly 18 according to one aspect of the present invention is shown. The needle actuator assembly 18 includes a needle actuator body 62 having guide surfaces 64, a needle shuttle 102 having cam surfaces 104 (shown in FIG. 11), and the needle 28 received by the needle shuttle 102 and configured to be in fluid communication with the container 14 through the fluid path assembly 200 (shown in FIG. 12). The needle actuator body 62 is generally rectangular with the guide surfaces 64 protruding radially inward. The needle shuttle 102 is received within the needle actuator body 62. The needle actuator body 62 is moveable within the housing 20, as the system transitions from the pre-use position (shown in FIGS. 2 and 3), an initial actuation position (FIG. 4), a use position (FIGS. 5 and 6), and a post-use position (FIGS. 7 and 8). The needle actuator body 62 is biased from the pre-use position to the post-use position via a biasing member, such as an extension spring 106, although other suitable biasing arrangements may be utilized. The needle actuator body 62 is released and free to move from the pre-use position to the use position upon engagement of the actuator button 26 and engagement with the drive mechanism 12 and restriction member 86 as discussed herein.

The needle shuttle 102 is moveable along a vertical axis between a retracted position where the needle 28 is positioned within the housing 20 and an extended position where at least a portion of the needle 28 extends out of the housing 20. The needle shuttle 102 is configured to move between the retracted position and the extended position through engagement between the guide surfaces 64 of the needle actuator 62 and the cam surfaces 104 (shown in FIG. 11) of the needle shuttle 102. As shown, for example, in FIG. 11, the cam surface(s) 104 is provided by first and second cam members 108, 110, with the first cam member 108 spaced from the second cam member 110. The housing 20 includes a guide post having recess configured to receive a T-shaped projection 114 on the needle shuttle 102, although other shapes and configurations may be utilized for the guide post and T-shaped projection 114. The needle shuttle 102 moves along the guide post between the retracted and extended positions. The guide post 112 is linear and extends about perpendicular from the housing, although other suitable arrangements may be utilized. The guide surfaces 64 of the needle actuator body 62 may be non-linear and may each include a first side and a second side positioned opposite from the first side.

The guide surfaces 64 of the needle actuator body 62 cooperate with the cam members 108, 110 of the needle shuttle 102 to move the needle shuttle 102 vertically between the retracted and extended positions as the needle actuator body 62 moves axially from the pre-use position to the post-use position. The needle shuttle 102 also includes a shuttle biasing member 120 configured to engage the housing 20 or the actuator button 26. In particular, the shuttle biasing member 120 engages the housing 20 or actuator button 26 and provides a biasing force when the needle actuator body 62 is transitioning from the use position to the post-use position.

As shown in FIGS. 7 and 8, when the needle actuator body 62 is fully transitioned to the post-use position, the cam members 108, 110 (shown in FIG. 11) of the needle shuttle 102 are disengaged from the guide surfaces 64 of the needle actuator body 62 and the shuttle biasing member 120 biases the needle shuttle 102 downward such that the needle 28 engages the pad 38, as discussed above. The needle actuator body 62 may interact with the actuator button 26 to prevent the actuator button 26 from popping back up until the post-use position is reached.

Fluid Path Assembly

As shown in FIG. 12, the injector device 2 also includes the fluid path assembly 200. In general, the fluid path assembly 200 includes the elements of the injector device 2 that contact the medicament fluid plus the tube crimping mechanism 202 (shown in FIGS. 13-19). For example, the fluid path assembly 200 can include portions of the container 14 (shown in FIGS. 1-10), the stopper 34 (shown in FIGS. 2-10), the valve assembly 16, and an adapter for connecting the container 14 with the valve assembly 16. The fluid path assembly 200 also includes the connecting tube 210 (shown in FIG. 12), a port or needle hub 212 for connecting the tube 210 to the needle shuttle 102, and the needle 28. The fluid path assembly 200 can be provided separately from other components of the injector device 2 and can be inserted into the injector device 2 prior to use. In that case, the fluid path assembly 200 can be provided with a disposable retainer for holding the components of the fluid path assembly 200 prior to installation in the bottom cover 24 of the housing 20.

To install or assemble the fluid path assembly 200 into the housing 20, the installer unwinds the flexible tube 210 from the disposable retainer. The installer then connect the needle hub or port 212 to an end of the tube 210 and connects the other end of the tube 210 to the container 14 and/or valve assembly 16. The installer then secures the needle hub or port 212 at the end of an arm portion of the needle shuttle 102 and inserts the container 14 and valve assembly 16 into the respective portions of the bottom cover 24 of the housing 20. The installer then positions or secures portions of the tube 210 against a top surface 214 of the needle actuator body 62, as shown in FIG. 12. It is noted that the valve module is not physically linked to the primary container, as the fluid path of the valve module is a sub-assembly and is assembled into the bottom case, which can be done independently of the assembly of the primary container.

Tube Crimping Arrangement

Figure 13:
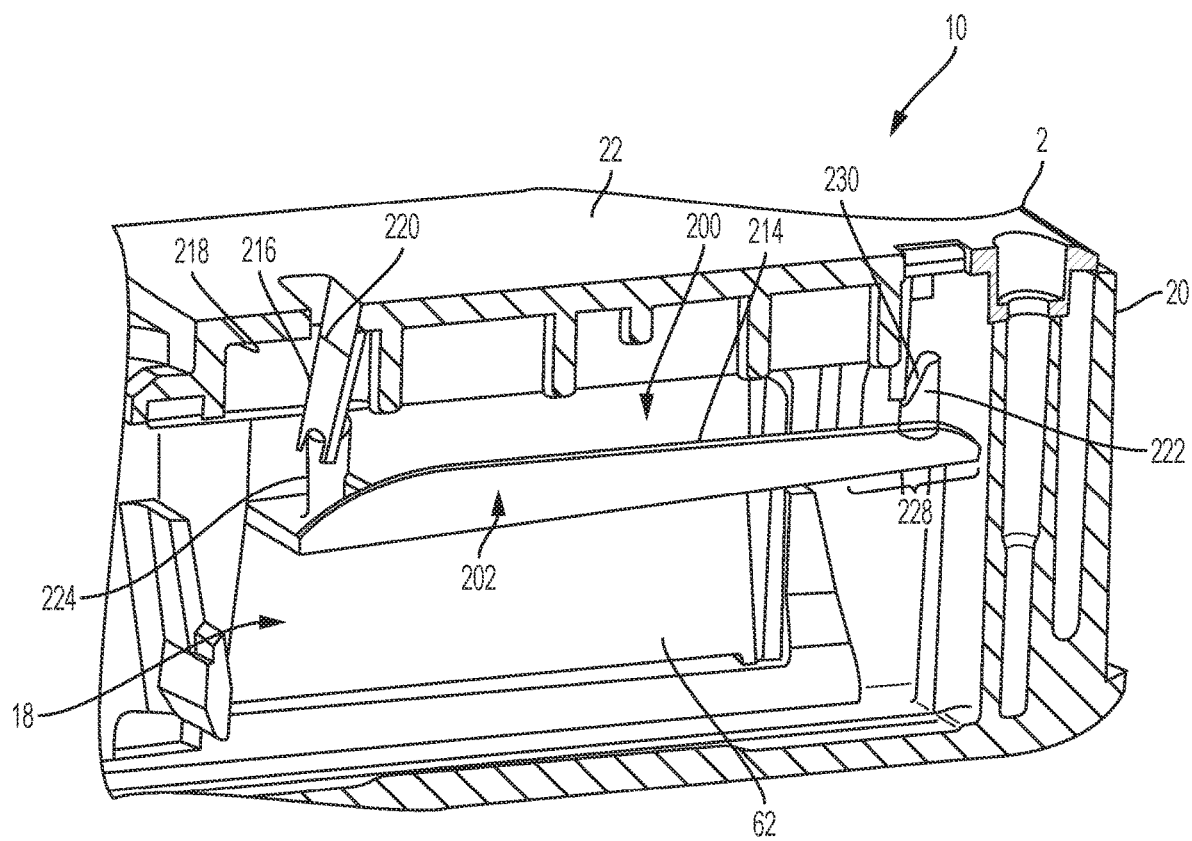
FIG. 13 is a cross-sectional view of a portion of a drug delivery system including a tube crimping arrangement according to an aspect of the present invention.
Figure 14:
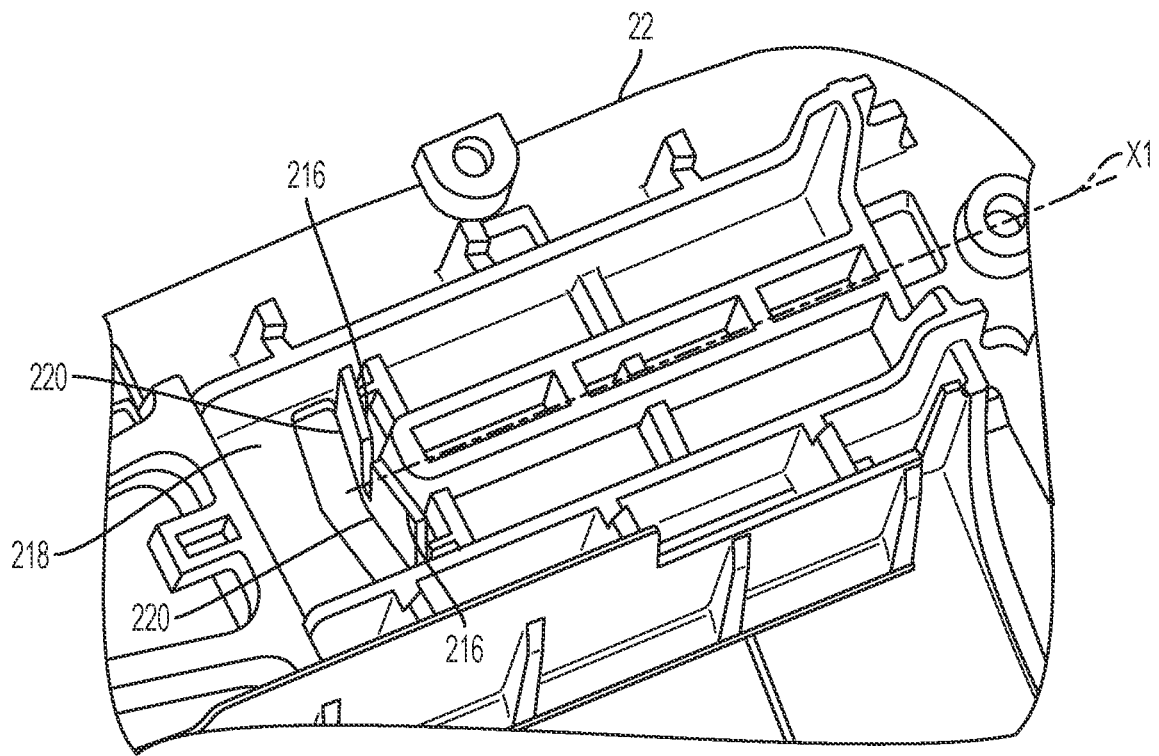
FIG. 14 is a perspective view of a portion of an interior surface of a top cover of the drug delivery system of FIG. 13 according to an aspect of the invention.
Figure 17:
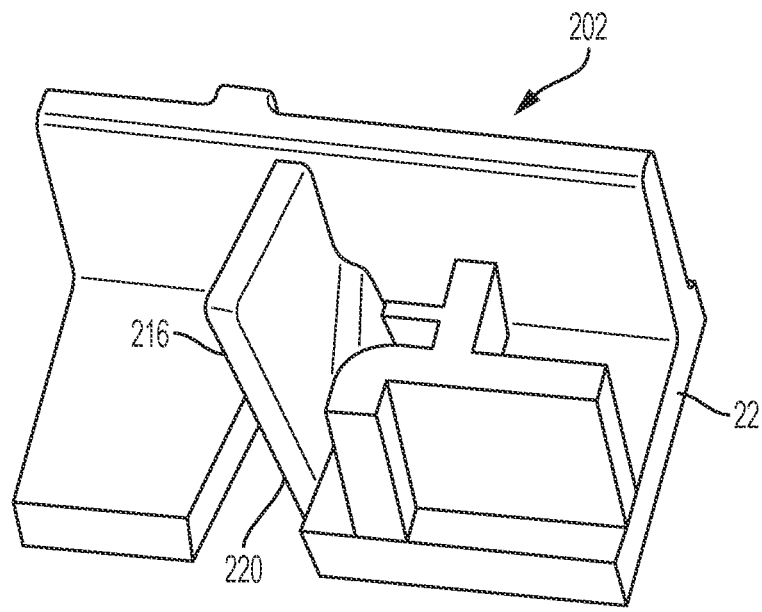
FIG. 17 is a perspective view of a portion of an interior surface of the top cover of the drug delivery system of FIG. 13 according to an aspect of the present invention.
Figure 18:
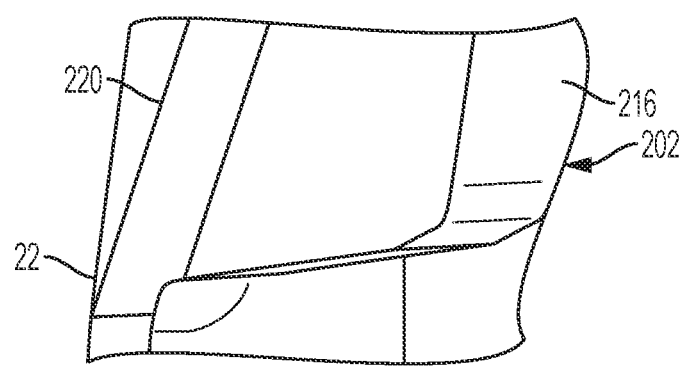
FIG. 18 is another perspective view of a portion of an interior surface of the top cover of the drug delivery system of FIG. 13 according to an aspect of the present invention.
Figure 19:
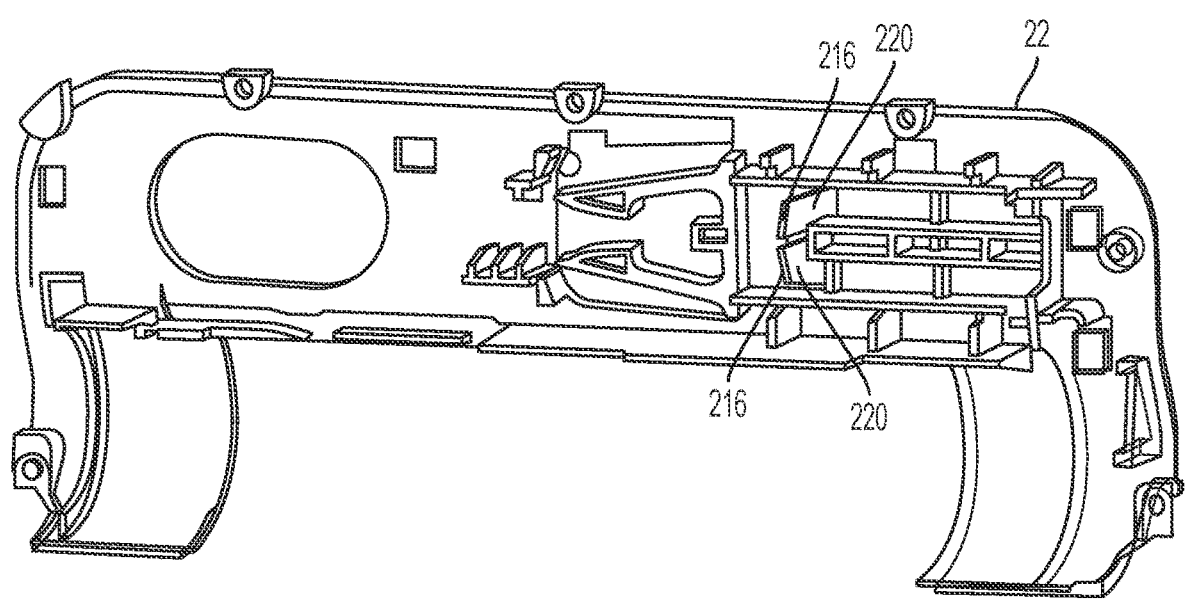
FIG. 19 is a perspective view of the interior surface of the top cover of the drug delivery system of FIG. 13 according to an aspect of the present invention.

With reference to FIG. 13, the top case also includes structures for crimping the tube 210 (shown in FIG. 12) to produce a fluid-block in the tube 210 as the injector device 2 transitions to the post-use or end of dose position. Collectively, these structures are referred to herein as the tube crimping arrangement 202. In some examples, as shown in FIGS. 13 and 14, the tube crimping arrangement 202 includes one or more crimping members configured to be driven toward a portion of the tube 210 by movement of the needle actuator assembly 18. As discussed herein, the needle actuator assembly 18 is released to travel to the post-use state by the button and then drive assembly 12 and restriction member (shown in FIGS. 2-8) and translates through the housing 20 to extend and retract the needle 28 (shown in FIGS. 2-8). In some examples, the crimping members are flexible fins or blades 216 extending from an interior surface 218 of the top cover 22 of the housing 20. A molded living hinge 220 can be disposed along the base of the fins or blade 216 to allow the fins or blades 216 to rotate or pivot towards the tube 210. Additional views of the top cover 22 of the housing and blades 216 are shown in FIGS. 17-19. In some examples, flexible blades 216 can be provided in a side-by-side arrangement to form a swinging gate as shown, for example, in FIGS. 14 and 19. The tube 210 is pushed into the gap between the opposing fins or blades 216, such that, when the blades 216 are driven together as the device 2 transitions to the post-use position, the tube 210 is clamped or compressed between the blades 216. The flexible blades 216 can be angled relative to the axis X1 of the top cover 22 of the housing 20, such that the blades 216 both bend and pivot toward the tube 210. For example, the blades 216 can be angled by about 10 degrees so that the blades 216 move both axially and radially inwardly toward the tube 210.

Figure 15:
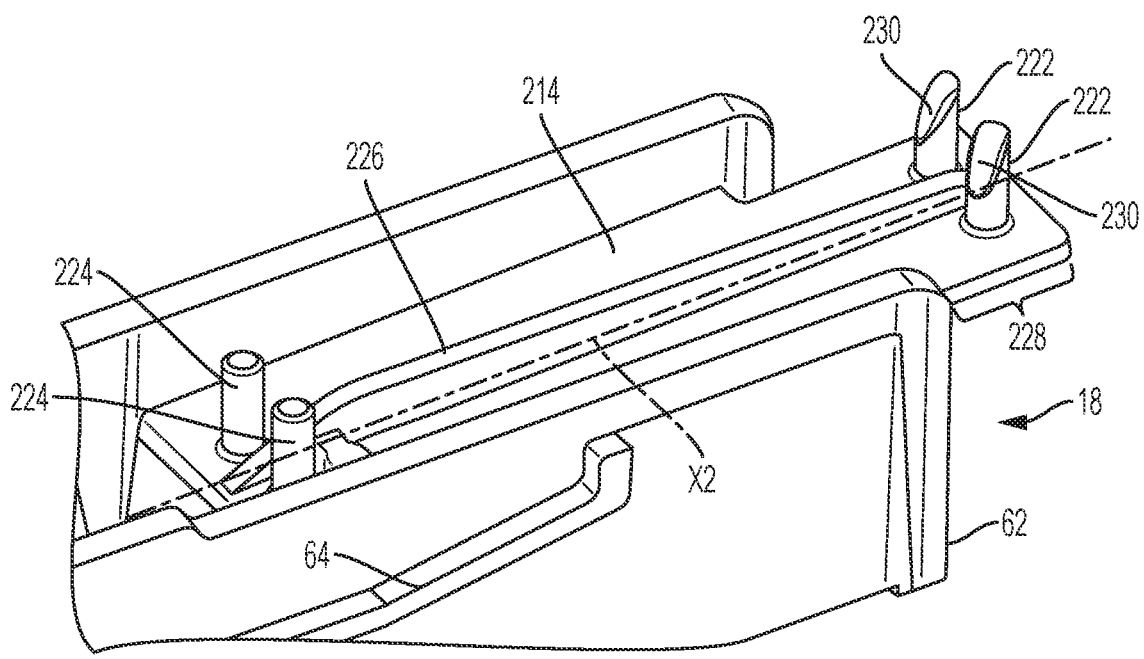
FIG. 15 is a perspective view of a portion of the needle actuator assembly of the drug delivery system of FIG. 13 according to an aspect of the present invention.
Figure 16:
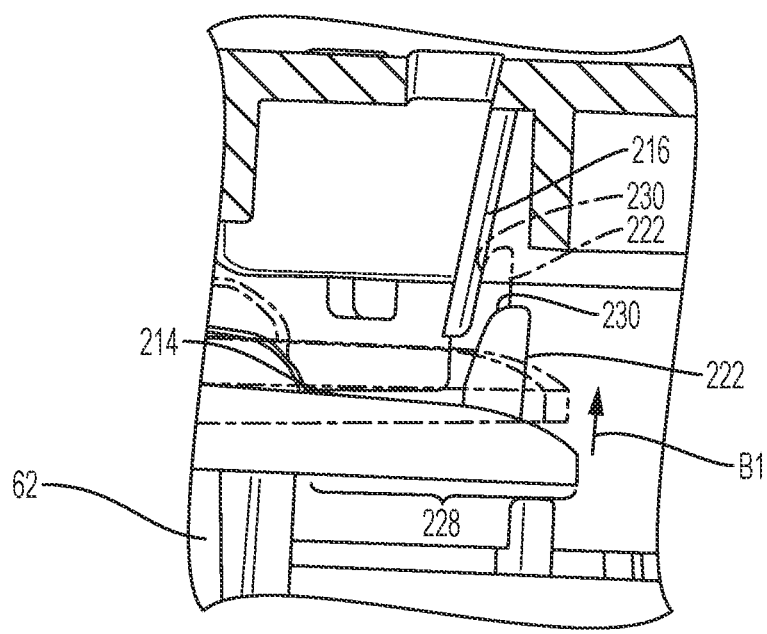
FIG. 16 is another cross-sectional view of the drug delivery system of FIG. 13 according to an aspect of the present invention with the system in a post-use position.

As shown in FIGS. 13, 15, and 16, the flexible blades 216 can be configured to be driven by protrusions, such as pins 222, 224, extending from a top surface 214 of the needle actuator body 62. The pins 222, 224 are positioned such that as the needle actuator body 62 translates through the housing 20, the pins 222, 224 contact the flexible blades 216, causing the blades 216 to cinch or clamp around the tube 210 to block fluid flow therethrough.

In some examples, the top surface 214 of the actuator body 62 includes two pairs of pins (e.g., front pins 222 and rear pins 224) disposed on the top surface 214 of the needle actuator body 62 and positioned to contact the blades 216 in a sequential fashion. The top surface 214 of the needle actuator body 62 can also include a ridge 226 (shown in FIG. 15) extending along the surface between the front pins 222 and the rear pins 224. In some cases, front pins 222 can be disposed on an extension portion 228 of the top surface 214 so that the spacing between the pins 222, 224 is sufficient to crimp the tube 210 in the desired manner. The front pins 222 can include angled surfaces 230 positioned to open or splay apart the blades 216 as shown, for example, in FIG. 16. The angled surfaces 230 can be angled relative to the longitudinal axis X2 (shown in FIG. 15) of the needle actuator body 62, such that opposing blades 216 are pushed apart to increase the gap therebetween.

During actuation of the injector device 2, which is caused by depressing and/or translating the actuation button 26, the needle actuator body 62 is directed along the guide surface 64, such that a front portion of the needle actuator body 62 rocks up at one of its ends in the direction of arrow B1 in FIG. 16. As a result of the rocking motion, the front pins 222 are effectively lifted up to contact the flexible blades 216. For example, the angled surface 230 of the pins 22 can contact the blades 216 as discussed herein. Contact between the front pins 222 and flexible blades 216 causes the blades 216 to splay apart to expand the gap between the blades 216. As the gap between the blades 216 increases, the tube 210 is pushed up by the ridge 226 on the needle actuator body 62 and into the gap. In some examples, the gap can be about 0.5 mm prior to actuation of the injector device 2. The gap can be expanded to about 0.7 mm when the blades 216 are splayed apart by the front pins 222.

After the dose of fluid is delivered to the patient in the manner described hereinabove, the injector device 2 transitions from the use position to the post-use position. During the transition to the post-use position, the needle actuator body 62 translates through the housing 20 along the guide surface 64 to retract the needle 28. In some examples, the last movement (e.g., the last few millimeters of movement) of the needle actuator body 62 along the guide surface 64 causes the rear pins 224 to deflect the flexible blades 216 forward and radially inward causing the blades 216 to pinch or clamp against the flexible tube 210. Desirably, the force required to maintain the pinch or clamp of the tube 210, as a result of the pressure applied on the blades 216 from the rear pins 224, is minimized and, preferably is less than or equal to about 1 N.

Force exerted by the biasing member or extension spring 106 may be minimized in the following manner. Under force of the extension spring 106, the blades 216 may be moved a distance of 1 mm to 2 mm to minimize the gap between the blades 216. In this position, each blade 216 exerts a force of about 0.5 N on the tube needle actuator body 62, meaning that a total force of about 1 N is provided by the needle actuator body 62 and the extension spring 106. Movement of the blades 216 to clamp or cinch the tube 210 causes the tube 210 to compress, which produces a transverse or side load on the tube 210. The force of the transverse or side load can be about 3 N. As the blades rotate and flex inwards to pinch the tube the transverse or side loads increase but the axial force reduces, this reducing force must be provided through the blades 216 by the needle actuator body 62 and the extension spring 106. This reduction in force applied by the extension spring 106 for cinching or clamping the tube 210 suggests a toggling action. For example, the tube 210 can be positioned to permit over-centering or toggle action of the flexible blades 216 so that the residual force required by the needle actuator body 62 and extension spring 106 to maintain the cinch or clamp of the tube 210 is minimal.

It is believed that the 3 N transverse or side load is sufficient to seal off flow of a thin wall tube having a double wall thickness of about 0.7 mm. In other examples, a thick walled tube having a double wall thickness of about 1.3 mm may be used. However, when using a thick walled tube, slightly more force or compression may be required to seal off the flow through the tube. Care must also be taken to ensure that the living hinge 220 of the blades 216 maintains sufficient flexibility so that the blades 216 contact and cinch the tube 210. Element analysis demonstrates that maximum shear rate for the injection should be below 40,000. In some cases, injections performed using the drug delivery device should be performed slightly faster than standard injections to prevent the living hinge 220 on the flexible blades 216 from freezing off due to shear.

Additional Exemplary Tube Crimping Arrangements

Figure 20:
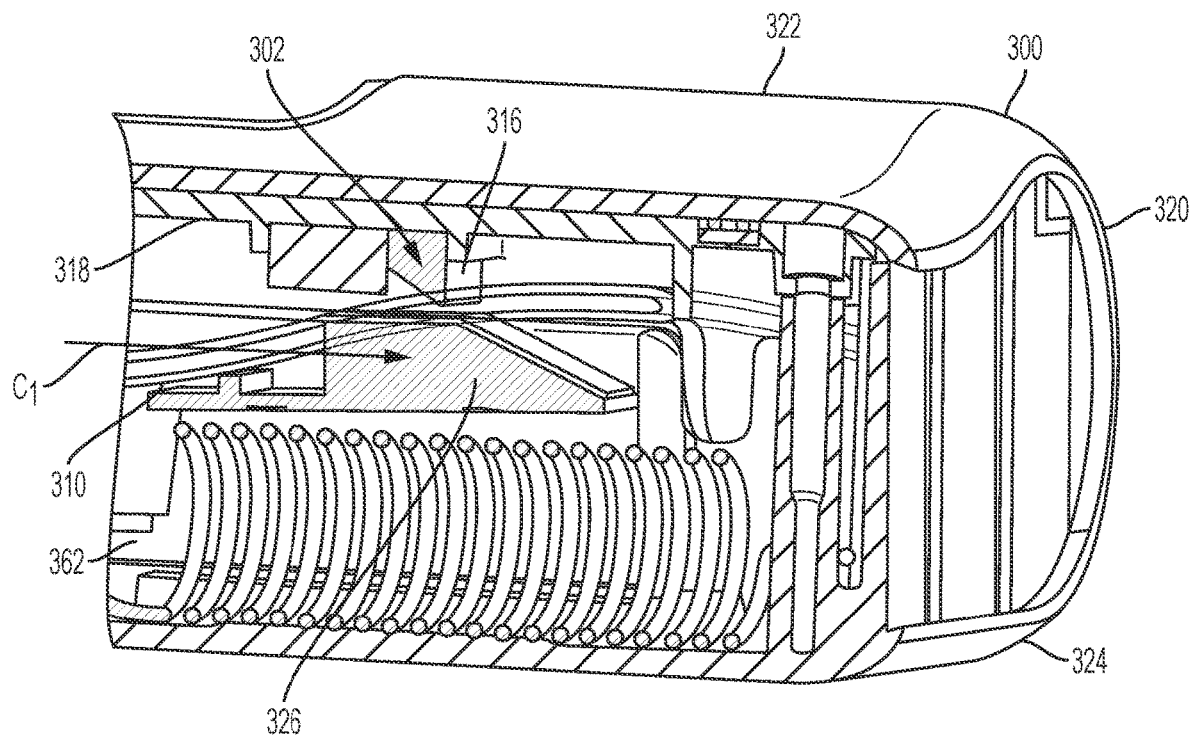
FIG. 20 is a cross-sectional view of a portion of another exemplary drug delivery system including a tube crimping arrangement according to an aspect of the present invention.
Figure 21:
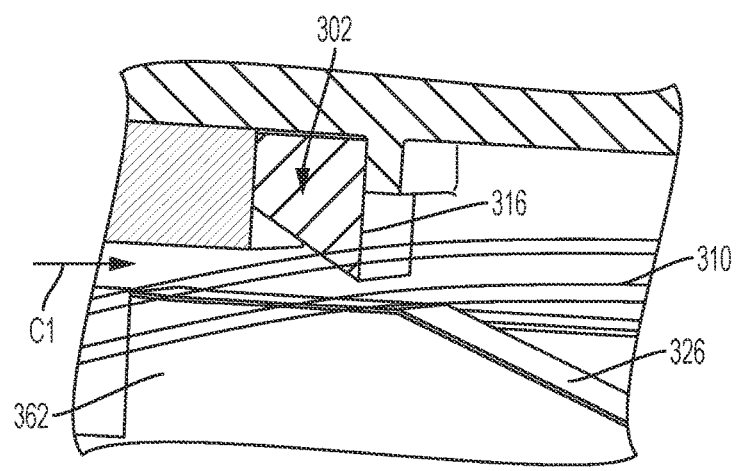
FIG. 21 is another cross-sectional view of a portion of the drug delivery system of FIG. 20 including a tube crimping arrangement according to an aspect of the present invention.

Another example of an injector device 300 with a tube crimping arrangement 302 for a flexible tube 310 is illustrated in FIGS. 20 and 21. As in previously described examples, the device 300 includes a housing 320 formed from a top cover 322 and bottom cover 324. The tube crimping arrangement 302 is simplified by replacing the pins and flexible blades of previously described embodiments with a sharp edge 316, which extends inwardly from an interior surface 318 of the top cover 322, and wedge 326 of a needle actuator body 362. The wedge 326 is positioned to drive the tube 310 toward the sharp edge 316 to compress the tube 310, thereby blocking fluid flow therethrough. As previously described, at the end-of-dose, the needle actuator body 362 translates through the housing 20 in the direction of arrow C1. Movement of the needle actuator body 362 through the housing 320 pushes the tube 310 toward the sharp edge 316. A small bore tube only requires about 1 mm of compression. As such, the needle actuator body 62 needs to move the tube 310 toward the sharp edge 316 by about 0.5 mm to close the gap between the wedge 326 of the needle actuator body 362 and the edge 316 of the top cover 322.

Figure 22:
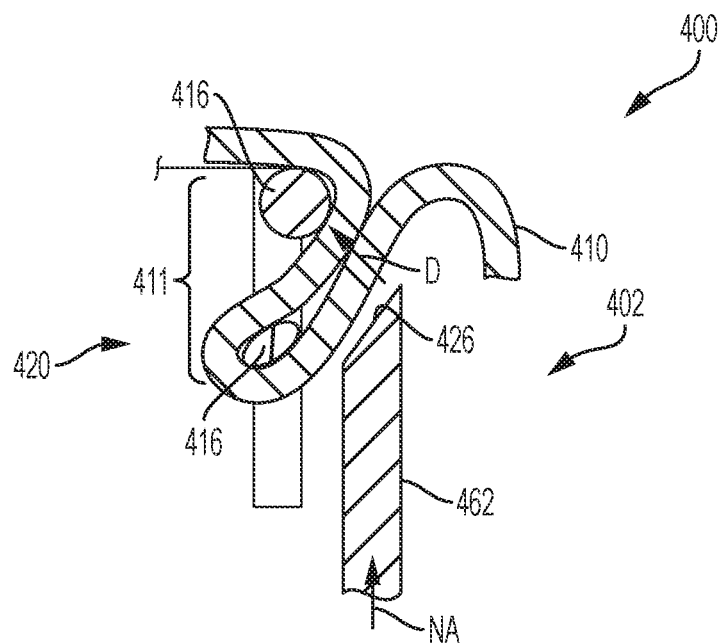
FIG. 22 is a schematic drawing of another exemplary drug delivery system including a tube crimping arrangement according to an aspect of the present invention.

Another example of an injector device 400 including a tube crimping arrangement 402 for a flexible tube 410 is illustrated in FIG. 22. The tube crimping arrangement 402 can be configured to kink the tube 410 to block fluid flow therethrough. The tube 410 can be placed in a housing 420 of the injector device 400 such that a portion 411 of the tube 410 is curved about guide structure(s) 416 to impart a bend to the tube 410. For example, the guide structure(s) 416 can be posts or protrusions which direct the tube 410 in a curved path. As a needle actuator body 462 translates through the housing 420 at end-of-dose, a portion 426 of the needle actuator body 462 is pressed against the curved portion 411 of the tube 410 to place a kink in the tube 410. Specifically, the curved portion 411 of the tube 410 is pressed, in the direction of arrow D, against the guide structure 416 to produce the kink.

Figure 23:
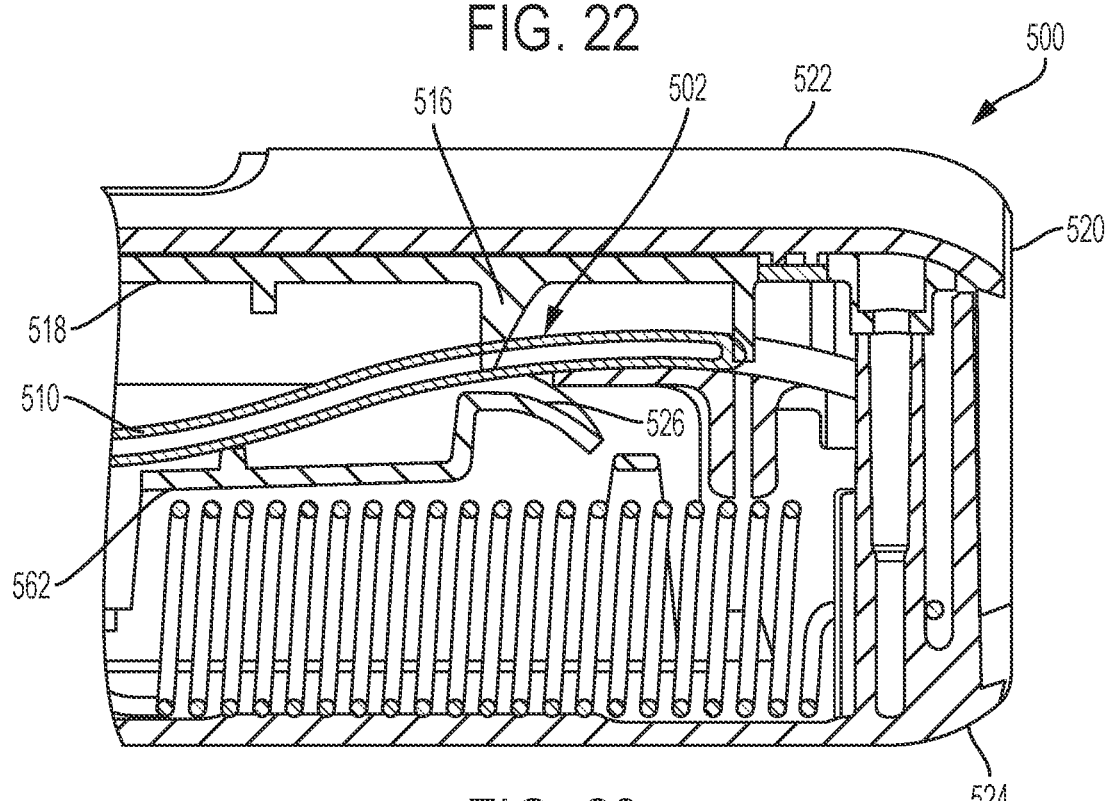
FIG. 23 is a cross-sectional view of a portion of a drug delivery system including another exemplary tube crimping arrangement according to an aspect of the present invention.
Figure 24B:
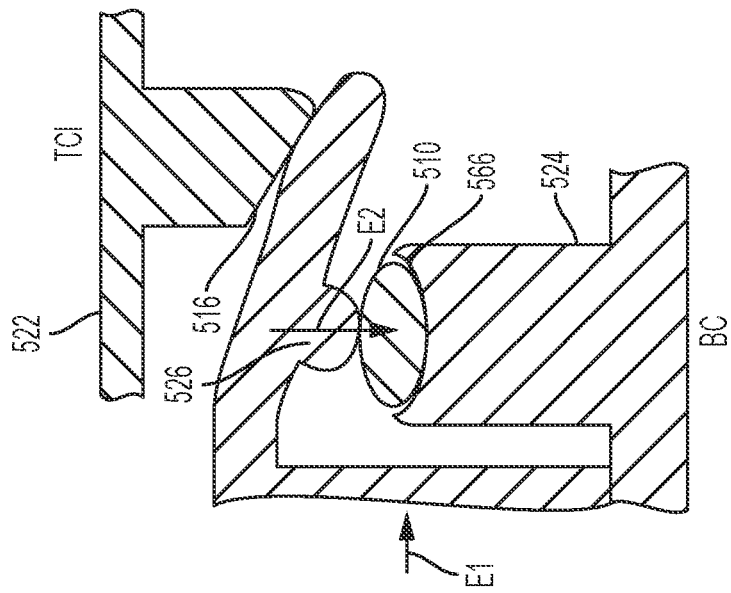
FIGS. 24A and 24B are schematic drawings of a similar tube crimping arrangement as shown in FIG. 23 according to aspects of the present invention.
Figure 24A:
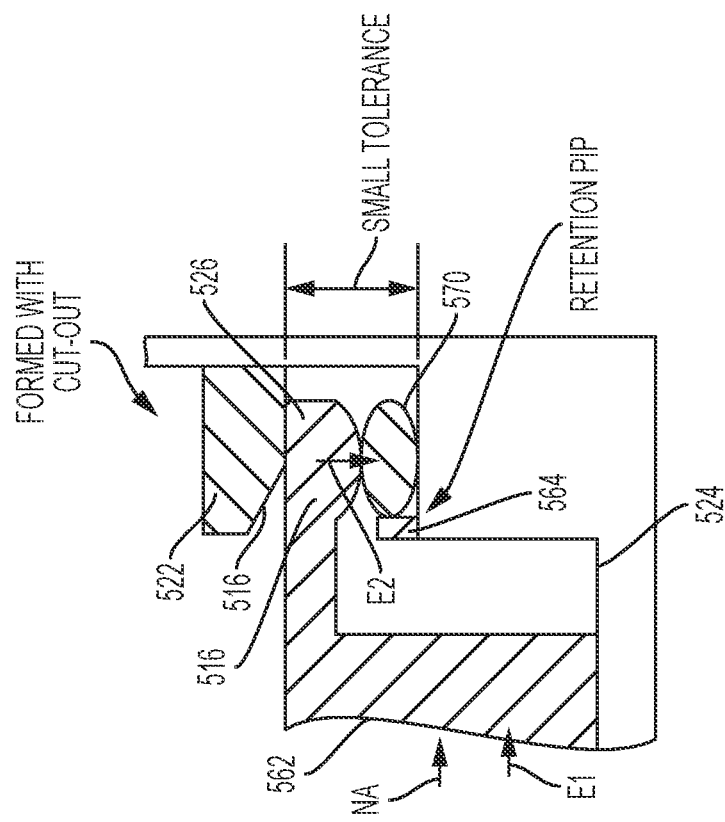

Another example of an injector device 500 including a tube crimping arrangement 502 for a flexible tube 510 is illustrated in FIGS. 23-24B. As shown in FIG. 23 and as previously described, the injector device 500 includes a housing 520 formed from a top cover 522 and a bottom cover 524. The tube crimping arrangement 502 may include a wedge shaped portion 516 extending from an inner surface 518 of the top cover 522 of the housing 520. A needle actuator body 562, which translates through the housing 520 as the injector device 500 transitions to the post use position, may include a pinching portion 526 configured to press against the tube 510. Specifically, as shown in FIGS. 24A and 24B, as the needle actuator body 562 is driven through the housing 520 in the direction of arrow E1, the wedge 516 directs the pinching portion 526 of the needle actuator body 562 toward the tube 510, in the direction of arrow E2. The movement of the needle actuator body 562 compresses the tube 510 against a portion of the bottom cover 524 of the housing 520. In some examples, the bottom cover 524 can include a protrusion 564 (shown in FIG. 24A) or retention structure for maintaining the position of the tube 510 when the pinching portion 526 of the needle actuator body 562 is pressed against it. In other examples, the bottom cover 524 can include a curved surface 566 (shown in FIG. 24B) or depression for receiving the tube 510. Other pinching or camming structures for compressing the tube 510 as the needle actuator body 562 translates through the housing 520 may also be constructed within the scope of the present disclosure, as will be apparent to those of ordinary skill in the art.

Figure 25:
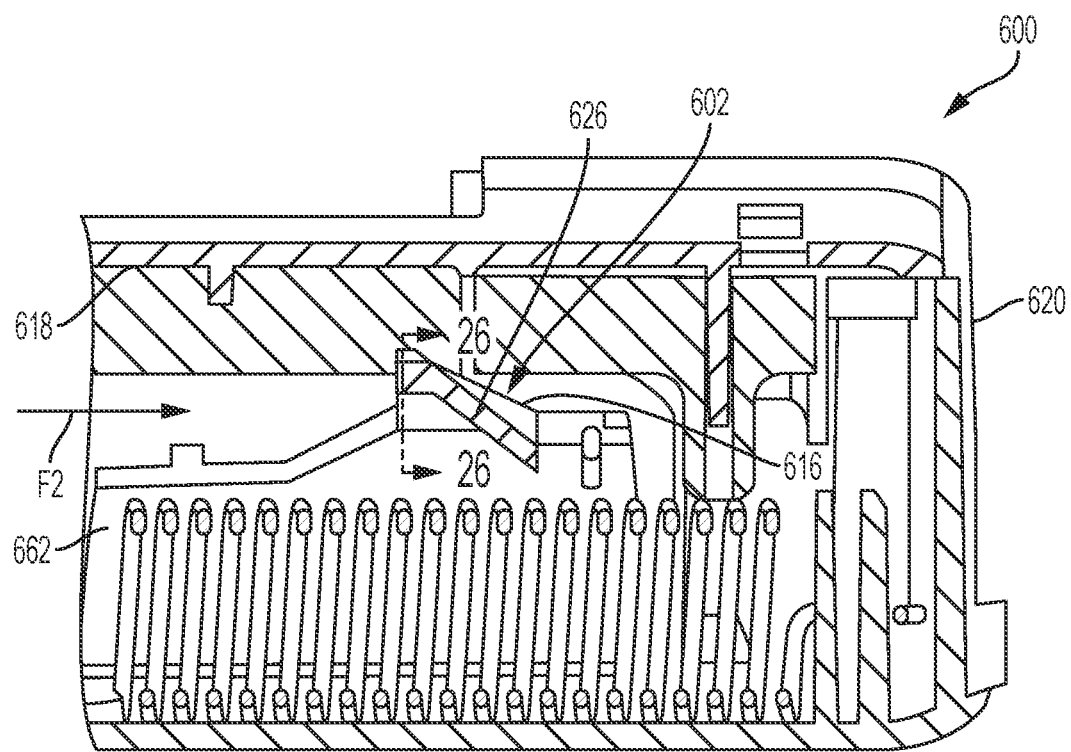
FIG. 25 is a cross-sectional view of a portion of a drug delivery system including another exemplary tube crimping arrangement according to an aspect of the invention.
Figure 26:
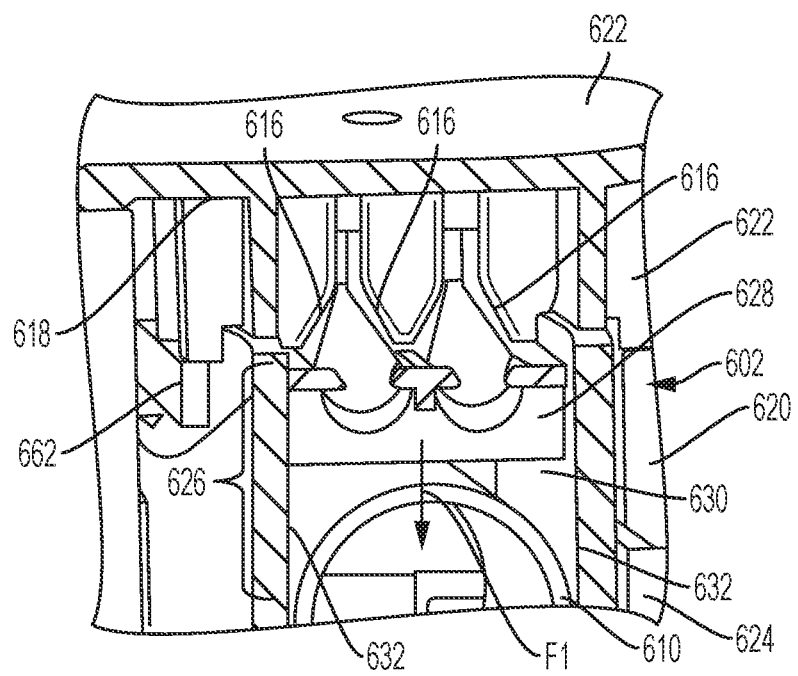
FIG. 26 is another cross-sectional view of a portion of the drug delivery system of FIG. 25 taken at line 26 according to an aspect of the present invention.

Another example of an injector device 600 including a tube crimping arrangement 602 for a flexible tube 610 is shown in FIGS. 25 and 26. As in previously described examples, the injector device 600 includes a housing 620 formed from a top cover 622 and a bottom cover 624. A needle actuator body 662 is disposed in the housing 620 and configured to translate through the housing 620 as the device 600 transitions from its use position to a post-use position. The tube crimping arrangement 602 includes a clamp 626 extending from the needle actuator body 662. As shown in FIG. 26, the clamp 626 includes a channel 630 formed from opposing walls 632. Element 628 is a rigid feature of the needle actuator and the tube 610 is positioned with element 628 during use. When the needle actuator moves to the post-use position, the tube is wedged up into the features on the top of the case thereby pinching the tube and blocking flow. These are two channels to accommodate two different pinches required for different inner tube diameters. The tube may be assembled in the one relating to its appropriate inner diameter during assembly.

Elements of one disclosed aspect can be combined with elements of one or more other disclosed aspects to form different combinations, all of which are considered to be within the scope of the present invention.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A drug delivery system for injecting a medicament, the system comprising:
   a container configured to receive a medicament;
   a drive assembly which, upon actuation, is configured to expel the medicament from the container;
   a needle for injecting the medicament to a patient;
   a needle actuator assembly comprising a movable portion biased by a biasing member and configured to move the needle between a pre-use position, a use position for delivery of the medicament to the patient, and a post-use position after delivery of the medicament is completed;
   a fluid path assembly comprising a tube in fluid communication with the container and the needle for conducting fluid from the container to the needle; and
   a tube crimping arrangement configured to engage the tube to block fluid flow through the tube,
   wherein after a dose of the medicament has been delivered to the patient through the needle, the drive assembly moves the movable portion of the needle actuator assembly to contact a portion of the tube crimping arrangement, which presses the tube crimping arrangement against the tube to at least partially restrict fluid flow through the tube.

2. The system of claim 1, wherein, upon actuation, the drive assembly automatically causes the tube crimping arrangement to restrict fluid flow through the tube.

3. The system of claim 1, further comprising a housing enclosing at least a portion of the container, drive assembly, needle, fluid path assembly, and tube crimping arrangement, the housing comprising a top cover engaged to a bottom cover.

4. The system of claim 1, further comprising a housing enclosing at least a portion of the container, drive assembly, needle, fluid path assembly, and tube crimping arrangement, wherein the needle is retracted into the housing in the pre-use and post use positions.

5. The system of claim 4, wherein at least a portion of the needle is extended from the housing in the use position.

6. The system of claim 1, wherein, upon actuation, the drive assembly automatically causes the needle actuator assembly to transition the needle between the use position and the post-use position.

7. A drug delivery system for injecting a medicament, the system comprising:
   a container configured to receive a medicament;
   a drive assembly which, upon actuation, is configured to expel the medicament from the container;
   a needle for injecting the medicament to a patient;
   a needle actuator assembly comprising a movable portion biased by a biasing member and configured to move the needle between a pre-use position, a use position for delivery of the medicament to the patient, and a post-use position after delivery of the medicament is completed;
   a fluid path assembly comprising a tube in fluid communication with the container and the needle for conducting fluid from the container to the needle; and
   a tube crimping arrangement configured to engage the tube to block fluid flow through the tube,
   wherein the drive assembly causes the tube crimping arrangement to engage the tube after a dose of the medicament has been delivered to the patient through the needle and wherein the tube crimping arrangement comprises at least one tube crimping member configured to be driven toward the tube by contact with the movable portion of the needle actuation assembly.

8. The system of claim 7, further comprising a housing enclosing at least a portion of the container, drive assembly, needle, and fluid path assembly, wherein the at least one crimping member comprises one or more flexible blades pivotally mounted to a portion of the housing.

9. The system of claim 8, wherein the movable portion of the needle actuator assembly comprises one or more protruding features extending therefrom, the protruding features being configured to contact the flexible blades to drive the flexible blades towards the tube.

10. The system of claim 7, further comprising a housing enclosing at least a portion of the container, drive assembly, needle, and fluid path assembly, and wherein the at least one crimping member comprises two flexible blades pivotally mounted to a portion of the housing and defining a gap therebetween.

11. The system of claim 10, wherein the movable portion of the needle actuator assembly comprises a first set of pins positioned to deflect the two flexible blades away from one another to expand the gap, and a second set of pins positioned to drive the two flexible blades towards one another to contact the tube.

12. The system of claim 11, wherein the movable portion of the needle actuator assembly comprises a ridge configured to press the tube into the gap, when the gap is expanded by contact between the first set of pins and the flexible blades.

13. The system of claim 7, wherein the biasing member of the needle actuator assembly exerts a force of 1N or less on the tube crimping arrangement.

14. A drug delivery system for injecting a medicament, the system comprising:
- a container configured to receive a medicament;
- a drive assembly which, upon actuation, is configured to expel the medicament from the container;
- a needle for injecting the medicament to a patient;
- a fluid path assembly comprising a tube in fluid communication with the container and the needle for conducting fluid from the container to the needle; and
- a tube crimping arrangement configured to engage the tube to block fluid flow through the tube,
- wherein the drive assembly causes the tube crimping arrangement to engage the tube after a dose of the medicament has been delivered to the patient through the needle and wherein the tube comprises a flexible single walled tube having a diameter of 0.7 mm or less.

* * * * *